United States Patent [19]

Jacques

[11] 4,339,601
[45] Jul. 13, 1982

[54] TEREPHTHALIC ACID DERIVATIVES AND PROCESS FOR PREPARING THEM

[75] Inventor: Albert M. V. Jacques, Norristown, Pa.

[73] Assignee: Union Carbide Corporation, Danbury, Conn.

[21] Appl. No.: 192,471

[22] Filed: Sep. 30, 1980

Related U.S. Application Data

[60] Division of Ser. No. 6,741, Jan. 26, 1979, Pat. No. 4,252,979, which is a continuation of Ser. No. 528,002, Nov. 29, 1974, abandoned.

[51] Int. Cl.³ .............................................. C07C 79/46
[52] U.S. Cl. .................................................. 562/438
[58] Field of Search .............................. 562/438, 479

[56] References Cited

PUBLICATIONS

Romanowski et al., Chem. Absts., 83, 27831(x), 1975.
Chen et al., Chem. Absts., 81, 135636(e), 1974.
Keith et al., Chem. Absts., 59, 15220(c), 1963.
Wagner et al., Synthetic Organic Chemistry, John Wiley and Sons, Inc., N.Y., p. 496, 1965.
Levy et al., Berichte, vol. 21 (1888), pp. 1463-1468 and pp. 1959-1964.

*Primary Examiner*—G. T. Breitenstein
*Attorney, Agent, or Firm*—W. E. Dickheiser

[57] ABSTRACT

The novel compounds of the formula:

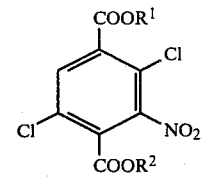

wherein $R^1$ and $R^2$ are each either hydrogen or an alkyl group containing from 1 to 4 carbon atoms, and maybe the same or different, are useful intermediates in a novel process for the preparation of herbicidally active compounds such as 2,5-dichloro-3-nitro-benzoic acid, 2,5-dichloro-3-amino-benzoic acid and their functional derivatives.

8 Claims, No Drawings

TEREPHTHALIC ACID DERIVATIVES AND PROCESS FOR PREPARING THEM

This application is a division of our prior U.S. application Ser. No. 006,741, filed Jan. 26, 1979, now U.S. Pat. No. 4,252,979, which is a continuation of application Ser. No. 528,002, filed Nov. 29, 1974, now abandoned.

BACKGROUND OF THE INVENTION 2,5-dichloro-3-amino-benzoic acid is an important selective herbicide, and is usually prepared by the reduction of the corresponding 3-nitro compound. However, it has proved difficult to prepare 2,5-dichloro-3-nitro-benzoic acid (itself a selective herbicide) to an acceptably high degree of purity, because the conventional preparations also give rise to other unwanted nitro isomers, which have to be separated from the desired product.

A widely used preparative route involves the nitration of 2,5-dichloro-benzoic acid or a derivative thereof, and whilst this yields the desired 3-nitro compound, significant amounts of the unwanted 6-nitro isomer are also formed and must be separated from the desired product. The separation of the unwanted isomer from the 3-nitro compound is a difficult, and therefore expensive, procedure.

This invention concerns new compounds, 2,5-dichloro-3-nitro-terephthalic acid and certain esters thereof, and a novel process for the preparation of 2,5-dichloro-3-nitrobenzoic acid involving these compounds, which avoids the problems of conventional processes.

In two articles dated 1888 (Berichte 21, 1467–1468 and 1959–1964), Levy and Andreocci describe processes purporting to prepare, amongst other products, 2,5-dichloro-3-nitroterephthalic acid and the dimethyl ester thereof. However, the physical and chemical properties of the products of their processes differ markedly from those of the relevant compounds prepared by methods described herein. The compounds that Levy and Andreocci prepared was not what they alleged them to be, but more probably 2,5-dichloro-3,6-dihydro-3-nitro-terephthalic acid and its dimethyl ester.

SUMMARY OF THE INVENTION

This invention relates to the novel compounds of the formula:

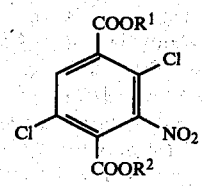

wherein $R^1$ and $R^2$ are independently either hydrogen or an alkyl radical containing from 1 to 4 carbon atoms. The invention also relates to processes for preparing these novel compounds, and to processes for converting them into the herbicidally active compound, 2,5-dichloro-3-nitrobenzoic acid.

DETAILED DESCRIPTION OF THE INVENTION

The novel compounds of the invention are 2,5-dichloro-3-nitro-terephthalic acid and certain mono- and diesters thereof. The esters are those wherein $R^1$ alone, $R^2$ alone or both of $R^1$ and $R^2$ are alkyl groups containing from 1 to 4 carbon atoms. It is preferred that when $R^1$ and $R^2$ are alkyl groups, they are straight chain alkyl groups-that is to say methyl, ethyl, n-propyl or n-butyl. The particularly preferred alkyl group is the methyl group.

The preferred compounds of the invention are those wherein $R^1$ and $R^2$ are both hydrogen or both methyl, that is to say:

2,5-dichloro-3-nitro-terephthalic acid; and
dimethyl 2,5-dichloro-3-nitro-terephthalate.

2,5-dichloro-3-nitro-terephthalic acid may be prepared by any suitable process. Most conveniently it is prepared by the hydrolysis of a corresponding mono- or diester, and preferably it is prepared from a mono- or diester of this invention. The conversion could be effected by acid hydrolysis, but it is preferred to use an alkaline hydrolysis, the ester being saponified to form an acid salt, and this acid salt than acidified to form the desired 2,5-dichloro-3-nitro-terephthalic acid.

The saponification is advantageously effected using an alkali metal base such as an alkali metal hydroxide, and the preferred saponification agent is sodium hydroxide. The saponification step is most conveniently carried out in an organic polar solvent, and preferred solvents are the lower alkanols, such as methanol and ethanol.

The product of the saponification is an acid salt, and this is converted to 2,5-dichloro-3-nitro-terephthalic acid by acidification, conveniently with a mineral acid, such as hydrochloric, nitric or sulphuric acid. A preferred mineral acid is concentrated hydrochloric acid.

The particularly preferred ester for use as the starting material in the preparation of 2,5-dichloro-3-nitroterephthalic acid is the dimethyl ester, and in a particularly preferred process this dimethyl ester is hydrolyzed to 2,5-dichloro-3-nitro-terephthalic acid using sodium hydroxide in aqueous ethanol, followed by acidification with concentrated hydrochloric acid.

The mono- and diesters of the invention may, of course, be prepared by any convenient process, but it is preferred that they be prepared by the nitration of the corresponding mono- and diesters of 2,5-dichloro-terephthalic acid. The nitration of 2,5-dichloro-terephthalic acid itself has been investigated, but found to be extremely difficult to effect because of the combined deactivating effect on the benzene ring of the two carboxyl groups and the two chloro groups. Surprisingly, it has now been discovered that by esterifying one or both of the carboxy groups the nitration of the benzene ring at the 3-position may be effected very easily, to give a good yield of the desired ester of 2,5-dichloro-3-nitroterephthalic acid. Any of the methods of nitration normally employed in organic chemistry may be used to form the 3-nitro compound, but the preferred method employs concentrated nitric acid in the presence of concentrated sulphuric acid as the nitrating mixture.

The mono- and diesters of 2,5-dichloro-terephthalic acid, used as starting materials for preparing the compounds of this invention, may themselves be prepared by any convenient standard methods, and the choice and performance of a suitable preparation for a particular compound is believed to be within the competence of one skilled in the art. However, by way of illustration, the following reaction scheme is given to show the steps involved in a preferred route to the diester of 2,5-dichloro-terephthalic acid:

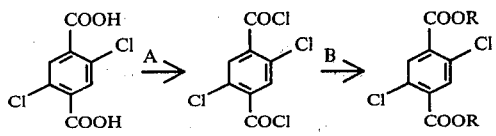

(wherein R is an alkyl group containing from 1 to 4 carbon atoms).

The di-(acid chloride) is most preferably formed in Step A by refluxing 2,5-dichloro-terephthalic acid with thionyl chloride to obtain the desired 2,5-dichloro-terephthaloyl chloride.

Step B of the reaction scheme, in which the di-(acid chloride) is converted to the diester, is most conveniently effected by reacting the di-(acid chloride) with the appropriate alcohol ROH to form the corresponding diester of 2,5-dichloro-terephthalic acid.

An alternative method of preparing the diester of 2,5-dichloro-terephthalic acid, that also provides a route to the monoesters and mixed esters, uses phase separation techniques to separate the various esters. In this method 2,5-dichloro-terephthalic acid is refluxed with an appropriate alcohol $R^3OH$ (wherein $R^3$ is alkyl having 1 to 4 carbon atoms) in an organic solvent immiscible with water, such as ethylene dichloride, and in the presence of concentrated sulphuric acid. After refluxing, normal work-up procedures make it possible to isolate the diester:

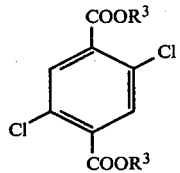

from the non-aqueous solvent layer, and the monoester:

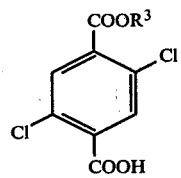

from the aqueous layer.

Having obtained the monoester by the above process, mixed esters may be obtained by reacting the monoester with an appropriate alcohol $R^4OH$ (wherein $R^4$ is alkyl having from 1 to 4 carbon atoms) to form the desired mixed diester:

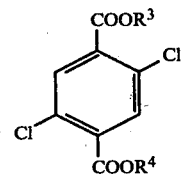

This invention also provides an improved process for the preparation of 2,5-dichloro-3-nitro-benzoic acid, which is an important compound both because of its herbicidal activity and because it is the precursor for 2,5-dichloro-3-amino-benzoic acid, itself an important herbicidally-active compound. The herbidical activity of 2,5-dichloro-3-nitro-benzoic acid and its functional derivatives is described in U.S. Pat. No. 3,013,873 (filed Nov. 19, 1957 in the names of Hart and Raman), the disclosure of which is incorporated herein by reference, and the herbidical activity of 2,5-dichloro-3-amino-benzoic acid, its functional derivatives and their preparation from the corresponding 3-nitro compounds, are described in U.S. Pat. Nos. 3,014,063 (filed Dec. 17, 1958 in the names of McLane, Bishop and Raman) and 3,174,842 (filed Sept. 6, 1961 in the same names), the disclosures of which are also incorporated herein by reference.

Thus, in a second aspect this invention provides a process for the preparation of 2,5-dichloro-3-nitro-benzoic acid, in which 2,5-dichloro-3-nitro-terephthalic acid is decarboxylated by heating with a suitable decarboxylating agent.

The preferred decarboxylating agents for use in this invention are dimethyl sulphoxide (DMSO) and dimethyl formamide (DMF). These reagents have been found to give the highest yields of 2,5-dichloro-3-nitro-benzoic acid, and their use is also advantageous since they each act as solvents for the reaction mixture, obviating the need for any other solvent.

However, it may be preferred in some instances to employ a separate solvent in addition to the decarboxylating agent. It has been found that preferred solvents, particularly when the decarboxylating agent is DMSO, are glycol dialkyl ethers, and the especially preferred glycol dialkyl ethers are ethylene glycol dimethyl ether (glyme) and diethylene glycol dimethyl ether (diglyme). By using glyme or diglyme as solvent it has been found possible to reduce the amount of decarboxylating agent without causing any reduction in the yield of the decarboxylation process.

The amount of decarboxylating agent used in the decarboxylation to form 2,5-dichloro-3-nitro-benzoic acid is naturally dependent on the amount of 2,5-dichloro-3-nitro-terephthalic acid to be decarboxylated, the other reagents present and the reaction conditions employed. However, by way of general indication it may be said that, where no other solvent is employed, the ratio of decarboxylating agent to 2,5-dichloro-3-nitroterephthalic acid is typically in the range of from about 50:1 to about 20:1. When separate solvent is also employed this ratio may be reduced to as low as 2:1, or even lower in some solvent systems. In any one particular case the optimum conditions are most usually, and most conveniently, determined empirically, and such empirical testing is believed to be within the competence of one skilled in the art.

The temperature at which the carboxylation is carried out is also dictated by the reagents used in the reaction; the decarboxylation may be carried out at reflux, but good yields have been obtained at reaction temperatures below reflux temperatures. By way of illustration, with the solvents and reagents most frequently employed the reaction temperature will usually lie in the range of about 80° C. to about 200° C., and a particularly convenient temperature is about 100° C. However, in some instances it may be desirable to use a reaction temperature outside that range.

It has also been found that the decarboxylation process of this invention, in some instances, may be further improved by the addition of alkali metal salts to the reaction mixture. The effect of the addition of such alkali metal salts may be to increase the yield of the decarboxylated product and/or to moderate the reaction conditions (lower the reaction temperature and shorten the reaction time) necessary to produce the desired product.

The preferred alkali metal salts are the alkali metal halides, and particularly the chlorides. Especially preferred salts for improving the yield of the decarboxylation process are lithium chloride and sodium chloride.

When alkali metal salts are added to the reaction mixture, they are preferably added in amounts which give a molar ratio of 2,5-dichloro-3-nitro-terephthalic acid to alkali metal salt of from about 1:2 to about 2:1, and most preferably about 1:1.

The starting material for the decarboxylation, 2,5-dichloro-3-nitro-terephthalic acid, is naturally most advantageously prepared by a process as described hereinbefore.

One of the important advantages of the process for preparing 2,5-dichloro-3-nitro-benzoic acid according to the invention is that the problem of unwanted nitro isomers is removed. The nitration of an ester of 2,5-dichloro-terephthalic acid can occur at only two positions on the benzene nucleus. However, since the nitrated ester is thereafter hydrolyzed to the diacid, these two nitration positions ultimately give rise to the same product, and therefore any mono-nitration of the ester of 2,5-dichloro-terephthalic acid will give a useful product. This removes the lengthy and expensive isomer separation necessary in the prior art processes.

The hydrolysis of the mono-nitrated ester yields, as described hereinbefore, 2,5-dichloro-3-nitro-terephthalic acid, which is then decarboxylated to give 2,5-dichloro-3-nitro-benzoic acid. An important and surprising advantage of the process of the invention is that the decarboxylation is virtually totally specific in removing the 4-carboxyl group, with substantially no loss of the 1-carboxyl group, so giving an excellent and unexpectedly high yield of the desired 2,5-dichloro-3-nitro-benzoic acid.

The following examples are now given, though only by way of illustration, to show details of preferred materials, amounts, conditions and techniques which may be employed in the process of this invention.

EXAMPLE 1

Preparation of dimethyl 2,5-dichloro-3-nitroterephthalate

Step A: Dimethyl 2,5-dichloro-terephthalate 200 ml of thionyl chloride were added to 100.5 gms of 2,5-dichloro-terephthalic acid, and the mixture was heated to reflux. After ½ hour at reflux, a further 55 ml of thionyl chloride were added to the reaction mixture, and the reflux continued.

After a total of 9¾ hours refluxing, the reaction mixture was evaporated to dryness to give a yellow solid residue. This residue was heated until it melted, and then poured into one liter of methanol, with stirring. This caused an exothermic reaction, accompanied by evolution of hydrogen chloride. When the HCl evolution has ceased, the reaction mixture was heated to boiling to drive off all excess HCl, and 400 ml chloroform were added so as just to dissolve the solid material, and the solution was left to stand overnight to crystallize.

99.6 gms of dimethyl 2,5-dichloro-terephthalate were obtained in the form of white needles melting at 133°–135° C.

The structure of the product was confirmed by the infrared spectrum, and by GLC analysis.

Step B: Dimethyl 2,5-dichloro-3-nitro-terephthalate 419 ml of concentrated (98%) sulphuric acid was placed in a flask maintained at 26°–27° C. by a cooling bath. 138 ml of red fuming nitric acid was dripped into the sulphuric acid over a period of five minutes with agitation. This nitrating mixture was maintained at 26°–27° C. for 10 minutes, and then 186.2 gms of dimethyl 2,5-dichloro-terephthalate were added at 27°–32° C. in small portions over a period of 3¾ hours, so that each portion of ester dissolved before the next was added.

After all the ester had been added, the reaction mixture was agitated for a further 18 hours, after which time the resultant red-brown solution was quenched by pouring it into 6 liters of crushed ice. The resulting solids were filtered off, washed well with water and dried to give a pale yellow solid product. This was recrystallized from 1 liter of isopropanol to give 164.8 gms of dimethyl 2,5-dichloro-3-nitroterephthalate in the form of white needles melting at 92°–94° C., and insoluble in a saturated solution of sodium bicarbonate.

The product was identified as dimethyl 2,5-dichloro-3-nitro-terephthalate by its N.M.R. and infrared spectra, GLC and analysis. The GLC indicated that the product obtained was 93.0% pure, and therefore the yield was 71.3% of theoretical.

The I.R. spectrum showed peaks at:

| | |
|---|---|
| 5.78–5.82 μ | (aryl ester C=O) |
| 7.79–9.80 μ | (aryl ester C—O) |
| 8.35–8.65 μ | (4-COOMe and 1-COOMe) |
| 6.48 μ | (introduction of —NO$_2$) |

The I.R. spectrum showed the influence of the nitro group, and the absence of any acidic hydroxyl peaks indicated that the product was the diester.

Parr Bomb analysis indicated that the product contained 22.44% chlorine (theoretical chlorine % = 23.0%).

The N.M.R. spectrum of the product showed three distinct peaks. The first peak occurred at 8τ (480 cps downfield from TMS) while the other two occurred at 6.016τ and 6.125τ (239 cps and 232.5 cps downfield from TMS respectively.)

The ratio of the areas of these peaks was 1:3:3.

The spectrum may be interpreted as follows:

The first peak is assigned to the single hydrogen remaining on the aromatic ring at the 6 position. The location of this peak leaves no doubt that it is due to the resonance of an aromatic proton.

The two closely spaced peaks at 6.016τ and 6.125τ are due to the resonances of the methyl protons of the methyl esters. Each set of three protons absorbs at a slightly different resonance because the methyl groups are in slightly different magnetic environments. The methyl protons of the 4-carboxymethyl group are shielded somewhat (moved to a higher field) by the diamagnetic anisotropic effect of the 3-nitro group. The interactions of the pi electrons of the nitro group with the applied magnetic field induces a diamagnetic shielding of the methyl protons adjacent to it. Therefore the 4-carboxymethyl protons have a slightly greater chemical shift (higher $\tau$ value) than the methyl protons of the 1-carboxymethyl group.

The N.M.R. spectrum, together with the other properties of the product, conclusively shows that the compound obtained by nitration of dimethyl 2,5-dichloroterephthalate was dimethyl 2,5-dichloro-3-nitro-terephthalate.

EXAMPLE 2

Preparation of 2,5-dichloro-3-nitro-terephthalic acid 21.3 gms of dimethyl 2,5-dichloro-3-nitro-terephthalate were dissolved in 110 ml of 90–95% ethanol, then 11 gms of sodium hydroxide were added with agitation, and the mixture was refluxed for 2 hours. The reaction mixture was allowed to cool, and the formed precipitate was filtered off and washed in acetone.

The washed precipitate was made into a slurry with acetone, and to this slurry 13 ml of concentrated hydrochloric acid were added with agitation. After $\frac{1}{2}$ hour of stirring, the formed sodium chloride was filtered off, washing with acetone, and the filtrate was heated on a steam bath to remove the solvents. The concentrate was then air dried at 50° to 60° C., after which time 16.2 gms of 2,5-dichloro-3-nitro-terephthalic acid were obtained. The product was purified by recrystallizing from a H$_2$O/EtOH mixture to yield a white crystalline solid, melting at 287°–288° C. with decomposition, and completely soluble in saturated sodium bicarbonate solution.

The product was identified by means of analysis, infrared spectra and GLC.

The GLC indicated that the crude product was 92.2% pure, the preparation therefore giving a yield of 84% of the theoretical yield.

| Analysis | |
|---|---|
| Chlorine content: | Theoretical 25.32% |
| | Found 24.61% |
| Neutralization equivalent: | Theoretical 140.02 |
| | Found 142.66 |

The infrared spectrum showed peaks at:

| | |
|---|---|
| 3.2–4.0 μ | (strong acidic —OH) |
| 5.9 μ | (acid C=O) |
| 6.46 μ | (retention of —NO$_2$ group) |

Further evidence that the compound prepared was in fact 2,5-dichloro-3-nitro-terephthalic acid was confirmed by the decarboxylation (as described in the following examples) to give the known compound 2,5-dichloro-3-nitro-benzoic acid.

EXAMPLE 3

Preparation of 2,5-dichloro-3-nitro-benzoic acid by decarboxylation using DMSO 0.05 moles of 2,5-dichloro-3-nitro-terephthalic acid were refluxed in 2.11 moles of dimethyl sulphoxide (DMSO) at 189° C. for 70 minutes, after which the DMSO was removed by flash evaporation. The residue was dissolved in saturated sodium bicarbonate solution, which was extracted with chloroform to remove unwanted side-products. The aqueous phase was then acidified with 10% hydrochloric acid to complete precipitation and the resulting precipitate was filtered off, washed well with water and dried to give 88.5% crude yield of 2,5-dichloro-3-nitro-benzoic acid, melting at 214°–216° C.

The structure of the product was confirmed by analysis, infrared spectra and GLC. The properties of the product were also compared with those of an authentic sample of 2,5-dichloro-3-nitro-benzoic acid, and found to be identical.

GLC indicated that the product was 99.6% 2,5-dichloro-3-nitro-benzoic acid. Thus, the yield from the above process was 88.2% of the theoretical yield.

| Analysis | |
|---|---|
| Chlorine content: | Theoretical 30.05% |
| | Found 29.30% |
| Neutralization Equivalent: | Theoretical 236.02 |
| | Found 236.97 |

The infrared spectrum showed the following peaks:

| | |
|---|---|
| 3.2–4.0 μ | (acidic —OH) |
| 5.92 μ | (acid C=O) |
| 6.50 μ | (retention of —NO$_2$ group) |
| 7.35 μ | (NO$_2$ group) |

In addition, the change in substitution pattern on the ring was indicated by a change in the "fingerprint" region of the spectrum, above 10$\tau$.

EXAMPLES 4 TO 7

Preparation of 2,5-dichloro-3-nitro-benzoic acid by decarboxylation using DMSO.

The preparation as described in Example 2 was repeated for a variety of molar ratios of the reactants, reaction temperatures and times. The results are expressed in Table 1 below:

TABLE 1

| Results of Decarboxylations Using DMSO | | | | |
|---|---|---|---|---|
| EXAMPLE | 4 | 5 | 6 | 7 |
| 2,5-dichloro-3-nitro terephthalic acid (moles) (45% pure) | 0.003 | 0.01 | 0.01 | 0.01 |
| DMSO (moles) | 0.986 | 0.42 | 0.42 | 0.42 |
| Reaction Temperature (°C.) | 182–9 | 189 | 100 | 100 |
| Reaction Time (hours) | 3¼ | 1 | 1 | 5½ |
| Yield of 2,5-dichloro-3-nitro-benzoic acid (%) | 50.2 | 88.2 | 20.7 | 86.3 |

These results show that using a ratio of 42:1 DMSO starting material and refluxing for 1 hour gives an excellent yield of 2,5-dichloro-3-nitro-benzoic acid. Reducing the reaction temperature necessitates increasing the reaction time to obtain high yields.

EXAMPLES 8 TO 12

Preparation of 2,5-dichloro-3-nitro-benzoic acid by decarboxylation using DMSO in the presence of a metal salt The method as described in Example 3 was used in a number of preparations in which a metal salt was added to the reaction mixture to assist the decaboxylation. The results are given in Table 2 below:

TABLE 2

Decarboxylation of 2,5-Dichloro-3-nitro-terephthalic Acid Using DMSO in the Presence of a Metal Salt

| EXAMPLE | 8 | 9 | 10 | 11 | 12 |
|---|---|---|---|---|---|
| 2,5-dichloro-3-nitro-terephthalic acid (moles) | 0.01 | 0.01 | 0.01 | 0.01 | 0.0613 |
| DMSO (moles) | 0.42 | 0.42 | 0.42 | 0.42 | 2.57 |
| Metal Salt | LiCl | LiCl | NaCl | NaCl | NaCl |
| Metal Salt (moles) | 0.01 | 0.02 | 0.01 | 0.01 | 0.0613 |
| Reaction Temp. (°C.) | 100 | 100 | 100 | 170 | 100 |
| Reaction time (hours) | 1 | 1 | 1 | ¼ | 1 |
| Yield of 2,5-dichloro-3-nitro-benzoic acid (%) | 53.7 | 40.5 | 91.2 | 94.4 | 76.2 |

These results show that excellent yields of 2,5-dichloro-3-nitrobenzoic acid may be obtained at lower reaction temperatures and/or shorter reaction times by employing a metal salt.

EXAMPLES 13 TO 19

Preparation of 2,5-dichloro-3-nitrobenzoic acid by decarboxylation using DMSO in the presence of an additional solvent The method described in Example 3 was used in a series of preparations using DMSO in the presence of various additional solvents. The results are given in Table 3.

These results show that by employing a solvent such as diglyme or glyme in addition to the DMSO, the yields of 2,5-dichloro-3-nitrobenzoic acid may be further improved. The use of the additional solvent also makes it possible to reduce substantially the amount of DMSO employed whilst achieving excellent yields. For example, an 81.2% yield was obtained from a 2:1 DMSO to 2,5-dichloro-3-nitroterephthalic acid reaction mixture when 50 ml of diglyme were present, after refluxing at 162° C. for only 15 minutes.

TABLE 3

Decarboxylation of 2,5-dichloro-3-nitro-terephthalic acid using DMSO in the presence of an additional Solvent

| Example | 13 | 14 | 15 | 16 | 17 | 18 | 19 |
|---|---|---|---|---|---|---|---|
| 2,5-dichloro-3-nitro-terephthalic acid (Moles) | 0.01 | 0.01 | 0.01 | 0.01 | 0.01 | 0.01 | 0.01 |
| DMSO (Moles) | 0.42 | 0.42 | 0.25 | 0.25 | 0.25 | 0.02 | 0.01 |
| Metal Salt | NaCl | NaCl | NaCl | NaCl | NaCl | NaCl | NaCl |
| Metal Salt (Moles) | 0.01 | 0.01 | 0.01 | 0.01 | 0.01 | 0.01 | 0.01 |
| Reaction Temp. (°C.) | 85 | 100 | 85 | 100 | 162 | 162 | 162 |
| Reaction Time (hours) | 1 | 1 | 1 | 1 | ¼ | ¼ | ¼ |
| Solvent | Glyme | Diglyme | Glyme | Diglyme | Diglyme | Diglyme | Diglyme |
| Solvent (ml.) | 100 | 100 | 50 | 50 | 50 | 50 | 50 |
| Yield of 2,5-dichloro-3-nitro-benzoic acid (%) | 100 | 100 | 69.8 | 78.4 | 94.0 | 81.2 | 41.2 |

EXAMPLE 20

Preparation of 2,5-dichloro-3-nitro-benzoic acid by decarboxylation using DMF 0.0008 moles of 2,5-dichloro-3-nitro-terephthalic acid were refluxed for 1 hour in 0.334 moles of dimethyl formamide (DMF), after which time the reaction mixture was flash evaporated to remove most of the DMF. To the residue was added 60 ml of water with agitation, and an orange precipitate formed which was filtered off and washed. The precipitate was dissolved in approximately 50 ml of saturated sodium bicarbonate solution, refiltered and then extracted with chloroform. The aqueous phase was acidified with 10% hydrochloric acid to complete precipitation, and the resulting precipitate was filtered, washed and dried to give an 85% crude yield of 2,5-dichloro-3-nitro-benzoic acid. Subsequent GLC analysis showed it to be 95.8% pure; thus, the yield of the process was 79.5% of theoretical.

The structure of the product was confirmed by the methods described in Example 3.

EXAMPLES 21 TO 23

Preparation of 2,5-dichloro-3-nitrobenzoic acid by decarboxylation using DMF

The method described in Example 20 was used in a series of preparations of 2,5-dichloro-3-nitro-benzoic acid employing various reaction conditions. The results are given in Table 4.

TABLE 4

Decarboxylation Using DMF

| EXAMPLE | 21 | 22 | 23 |
|---|---|---|---|
| 2,5-dichloro-3-nitro-terephthalic acid (moles) | 0.008 | 0.0087 | 0.0087 |
| DMF (moles) | 0.334 | 0.353 | 0.353 |
| Metal Salt | NaCl | — | — |
| Metal Salt (moles) | 0.008 | — | — |
| Reaction Temperature (°C.) | 100 | 100 | 100 |
| Reaction Time (hours) | 1 | 1 | 2 |
| Yield of 2,5-dichloro-3-nitro benzoic acid (%) | 72.5 | 96.8 | 96.8 |

These results demonstrate the excellent yield of the desired product, 2,5-dichloro-3-nitro-benzoic acid, which may be obtained using DMF as the decarboxylation reagent.

EXAMPLE 24

Preparation of monoxethyl 2,5-dichloro-3-nitroterephthalate

Step A: Monomethyl 2,5-dichloro-terephthalate 36.9 gms of 2,5-dichloro-terephthalic acid, 37.6 ml of methanol, 4.7 ml of concentrated sulphuric acid and 100 ml of ethylene dichloride were refluxed together for 3 hours. The solution was filtered, and then warmed and a saturated sodium bicarbonate solution added to react with the acids present.

The aqueous phase was then washed twice with chloroform, separated and filtered to give a clear yellow solution. To this solution 10% hydrochloric acid was added to effect precipitation, and the formed white solid material was filtered off, washed and dried. The product was purified by recrystallizing from a water/ethanol mixture.

The white solid product obtained was further purified by dissolving it in chloroform, filtering and flash evaporating to dryness. Finally, a recrystallization from a mixture of water and a minimum amount of ethanol yielded 9.8 gms of monomethyl 2,5-dichloro-terephthalic acid in the form of glossy white flakes, melting at 169°–171° C.

Step B: Monomethyl 2,5-dichloro-3-nitro-terephthalate 2.4 ml of red fuming nitric acid were added to 6.5 ml of concentrated sulphuric acid at room temperature, and this nitrating mixture was stirred as 3.0 grams of monomethyl 2,5-dichloro-terephthalate were added in small increments over a period of ¾ hour. The mixture was then heated gently to about 55° C. to effect complete solution.

The solution was then quenched on 50 ml of crushed ice, and the formed solid product was filtered off, washed and dried. This product was recrystallized from a 4:1 water/ethanol mixture to yield 1.6 grams of monomethyl 2,5-dichloro-3-nitro-terephthalate as a white micro-crystalline solid, melting at 164°–170° C. The structure of the product was confirmed by GLC.

What is claimed is:

1. A process for the preparation of 2,5-dichloro-3-nitrobenzoic acid, which comprises heating 2,5-dichloro-3-nitro-terephthalic acid in the presence of a decarboxylating agent selected from the group consisting of dimethyl sulphoxide and dimethyl formamide.

2. The process of claim 1, wherein the ratio of decarboxylating agent to 2,5-dichloro-3-nitro-terephthalic acid is from about 50:1 to about 2:1.

3. The process of claim 1 wherein a glycol dialkyl ether is employed to act as a solvent.

4. The process of claim 3, wherein the glycol dialkyl ether is selected from the group consisting of:
   (a) glyme; and
   (b) diglyme.

5. The process of claim 1, wherein the decarboxylating agent is dimethyl sulphoxide.

6. The process of claim 1, wherein the decarboxylating agent is dimethyl formamide.

7. The process of claims 1, 5 or 6, wherein an alkali metal salt is employed to enhance the yield of the process.

8. The process of claim 7, wherein the metal salt is an alkali metal halide selected from the group consisting of:
   (a) sodium chloride; and
   (b) lithium chloride.

* * * * *